United States Patent
Taylor et al.

(10) Patent No.: US 8,460,368 B2
(45) Date of Patent: Jun. 11, 2013

(54) EXPANDABLE MEMBER FOR DEPLOYING A PROSTHETIC DEVICE

(75) Inventors: David M. Taylor, Lake Forest, CA (US); Philippe Marchand, Lake Forest, CA (US); Larry Wood, Rancho Santa Margarita, CA (US); Robert Bowes, Laguna Hills, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1135 days.

(21) Appl. No.: 12/396,378

(22) Filed: Mar. 2, 2009

(65) Prior Publication Data
US 2009/0228093 A1  Sep. 10, 2009

Related U.S. Application Data

(60) Provisional application No. 61/032,851, filed on Feb. 29, 2008.

(51) Int. Cl.
*A61F 2/24* (2006.01)

(52) U.S. Cl.
USPC ........................................................ 623/2.11

(58) Field of Classification Search
USPC .................. 623/1.11, 1.26, 2.1–2.19; 606/200
See application file for complete search history.

(56) References Cited

U.S. PATENT DOCUMENTS

| | | | |
|---|---|---|---|
| 3,409,013 A | 11/1968 | Berry | |
| 3,548,417 A | 12/1970 | Kisher | |
| 3,587,115 A | 6/1971 | Shiley | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 4,035,849 A | 7/1977 | Angell et al. | |
| 4,056,854 A | 11/1977 | Boretos et al. | |
| 4,106,129 A | 8/1978 | Carpentier et al. | |
| 4,222,126 A | 9/1980 | Boretos et al. | |
| 4,265,694 A | 5/1981 | Boretos et al. | |
| 4,297,749 A | 11/1981 | Davis et al. | |
| 4,339,831 A | 7/1982 | Johnson | |

(Continued)

FOREIGN PATENT DOCUMENTS

| | | |
|---|---|---|
| DE | 2246526 | 3/1973 |
| DE | 2056023 | 3/1981 |

(Continued)

OTHER PUBLICATIONS

Andersen, et al., Transluminal implantation of artificial heart valves. Description of a new expandable aortic valve and initial results with implantation by catheter technique in closed chest pigs. European Heart Journal (1992), 13, 704-708.

(Continued)

*Primary Examiner* — Gary Jackson
*Assistant Examiner* — Michael Mendoza
(74) *Attorney, Agent, or Firm* — David L. Hauser

(57) ABSTRACT

An apparatus for delivering a prosthetic device through the vasculature of a patient includes a radially expandable member coupled to the distal end of an elongate shaft. The expandable member has an open frame configuration and an outer mounting surface for mounting the prosthetic device in a collapsed state thereon. The expandable member expands radially outwards from a first configuration to a second configuration to expand a prosthetic device mounted thereon.

12 Claims, 15 Drawing Sheets

U.S. PATENT DOCUMENTS

| | | | |
|---|---|---|---|
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely |
| 5,554,185 A | 9/1996 | Block et al. |
| 5,571,175 A | 11/1996 | Vanney et al. |
| 5,591,185 A | 1/1997 | Kilmer et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian |
| 6,302,906 B1 | 10/2001 | Goecoechea et al. |
| 6,350,277 B1 | 2/2002 | Kocur |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle |
| 6,482,228 B1 | 11/2002 | Norred |
| 6,488,704 B1 | 12/2002 | Connelly et al. |
| 6,569,196 B1 | 5/2003 | Vesely et al. |
| 6,605,112 B1 | 8/2003 | Moll |
| 6,730,118 B2 | 5/2004 | Spenser et al. |
| 6,733,525 B2 | 5/2004 | Yang et al. |
| 6,830,584 B1 | 12/2004 | Seguin |
| 6,893,460 B2 | 5/2005 | Spenser et al. |
| 6,896,690 B1 | 5/2005 | Lambrecht et al. |
| 6,908,481 B2 | 6/2005 | Cribier |
| 7,018,406 B2 | 3/2006 | Seguin et al. |
| 7,276,078 B2 | 10/2007 | Spenser et al. |
| 7,276,084 B2 | 10/2007 | Yang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 2001/0021872 A1 | 9/2001 | Bailey et al. |
| 2002/0032481 A1 | 3/2002 | Gabbay |
| 2002/0111647 A1* | 8/2002 | Khairkhahan et al. ........ 606/200 |
| 2002/0173842 A1 | 11/2002 | Buchanan |
| 2003/0050694 A1 | 3/2003 | Yang et al. |
| 2003/0100939 A1 | 5/2003 | Yodfat et al. |
| 2003/0212454 A1 | 11/2003 | Scott et al. |
| 2004/0186565 A1 | 9/2004 | Schreck |
| 2004/0260389 A1 | 12/2004 | Case et al. |
| 2005/0234546 A1 | 10/2005 | Nugent et al. |
| 2006/0149350 A1 | 7/2006 | Patel et al. |
| 2006/0229719 A1 | 10/2006 | Marquez et al. |

FOREIGN PATENT DOCUMENTS

| | | |
|---|---|---|
| DE | 0103546 | 3/1984 |
| DE | 0144167 | 6/1985 |
| DE | 1271508 | 11/1986 |
| DE | 0597967 | 12/1994 |
| DE | 0592410 | 10/1995 |
| DE | 19532846 | 3/1997 |
| DE | 19546692 | 6/1997 |
| DE | 0850607 | 7/1998 |
| DE | 19857887 | 7/2000 |
| DE | 19907646 | 8/2000 |
| DE | 1057460 | 12/2000 |
| DE | 1088529 | 4/2001 |
| DE | 10049812 | 4/2002 |
| DE | 10049813 | 4/2002 |
| DE | 10049814 | 4/2002 |
| DE | 10049815 | 4/2002 |
| DE | 1570809 | 9/2005 |
| DE | 2788217 | 7/2007 |
| WO | WO 91/17720 | 11/1991 |
| WO | WO 92/17118 | 10/1992 |
| WO | WO 93/01768 | 2/1993 |
| WO | WO 97/24080 | 7/1997 |
| WO | WO 98/29057 | 7/1998 |
| WO | WO 99/33414 | 7/1999 |
| WO | WO 99/40964 | 8/1999 |
| WO | WO 99/47075 | 9/1999 |
| WO | WO 00/41652 | 7/2000 |
| WO | WO 00/47139 | 8/2000 |
| WO | WO 01/35878 | 5/2001 |
| WO | WO 01/49213 | 7/2001 |

| WO | WO 01/54625 | 8/2001 |
| WO | WO 01/62189 | 8/2001 |
| WO | WO 01/64137 | 9/2001 |
| WO | WO 01/76510 | 10/2001 |
| WO | WO 02/22054 | 3/2002 |
| WO | WO 02/36048 | 5/2002 |
| WO | WO 02/41789 | 5/2002 |
| WO | WO 02/43620 | 6/2002 |
| WO | WO 02/47575 | 6/2002 |
| WO | WO 02/49540 | 6/2002 |
| WO | WO 03/047468 | 6/2003 |
| WO | WO 2006/014233 | 2/2006 |
| WO | WO 2006/034008 | 3/2006 |
| WO | WO2007/135437 | 11/2007 |
| WO | WO 2008/005405 | 1/2008 |
| WO | WO 2008/147964 | 12/2008 |
| WO | WO 2008150529 | 12/2008 |

OTHER PUBLICATIONS

Andersen, Henning Rud, History of Percutaneous Aortic Valve Prosthesis, Herz 34, 2009, Urban & Vogel, pp. 343-346.
International Search Report mailed May 29, 2009 for International Patent Application No. PCT/US2009/035756, filed Mar. 2, 2009.

* cited by examiner

EXPANDABLE MEMBER FOR DEPLOYING A PROSTHETIC DEVICE

CROSS-REFERENCE TO RELATED APPLICATIONS

The present application claims the benefit of U.S. Provisional Application No. 61/032,851, filed Feb. 29, 2008, which is hereby incorporated by reference.

FIELD

The present invention relates generally to medical devices and methods. More particularly, the present invention provides minimally invasive methods and devices for percutaneous transcatheter implantation of expansible prosthetic heart valves within or adjacent a valved anatomic site within the heart.

BACKGROUND

When treating certain medical conditions, it is sometimes desirable to expand a frame or other radially expandable member in an orifice or conduit of a patient's body. For example, expandable tubes called stents are commonly inserted into a natural conduit of a patient's body and expanded inside the conduit to hold the conduit in an open position. Such expandable stents can be used to expand, widen, or otherwise provide structural support to various conduits of the human body, including, for example, arteries, veins, bile ducts, the esophagus, and the colon. In other treatment procedures, prosthetic heart valves that include a frame member are implanted into the body at a treatment site (e.g., a heart valve annulus). These prosthetic heart valves can be positioned in the heart valve annulus by expanding the frame member to roughly the size of the valve annulus.

Such frames or stents can be self-expanding or expanded using an expansion balloon. One conventional method involves positioning a frame on a balloon of a balloon catheter, maneuvering the balloon and frame to the treatment site, and inflating the balloon with a fluid to expand the frame or stent to the desired size. Such an approach, however, can have drawbacks. For example, during the expansion of the balloon the orifice or conduit is usually at least partially, if not completely, occluded, which can cause certain undesirable effects. Accordingly, it is desirable to provide methods and delivery systems that eliminate or reduce these and other potential drawbacks.

SUMMARY

In the deployment of prosthetic devices in the aortic arch or in the intracranial arteries, blockage of the lumen by the balloon during the implantation process, even for a short period of time, can introduce complications to the medical procedure. The apparatuses and methods described in various embodiments herein can reduce and/or substantially eliminate the occlusion of the lumen (e.g., artery or other passageway) during expansion of a prosthetic device therein.

The apparatuses and methods described in various embodiments herein can prolong prosthetic device deployment time, eliminate pacing and its associated risks, as well as permitting repositioning of the prosthetic device during deployment.

In one embodiment, an apparatus for delivering a prosthetic device through the vasculature of a patient comprises an elongate shaft having a distal end and a radially expandable member coupled to the distal end of the elongate shaft. The expandable member can comprise a distal end portion and a proximal end portion that are movable relative to one another between a first orientation and a second orientation. A plurality of struts can be coupled to at least one of the distal end and proximal end portions of the expandable member and can have a prosthetic device receiving area. In the first orientation the distal end and proximal end portions are a first distance apart, and in the second configuration the distal end and proximal end portions are a second distance apart. The second distance can be less than the first distance. Movement of the distal end and proximal end portions from the first orientation to the second orientation can cause connecting members to expand radially outwards from a first configuration to a second configuration to expand the prosthetic device In specific implementations, the expandable member can comprise a screw member that extends between the distal end portion and the proximal end portion, and rotation of the screw member can cause the distal end and proximal end portions to move from the first to the second orientation. In other specific implementations, the expandable member can comprise a wire that extends between the distal end portion and the proximal end portion, and movement of the wire can cause the distal end and proximal end portions to move from the first to the second orientation.

In other specific implementations, one or more of the plurality of struts can extend from the distal end portion to the proximal end portion. In other specific implementations, the expandable member can comprise a cover that at least partially surrounds the plurality of struts. In other specific implementations, the cover can be configured to open to permit fluid to flow through the expandable member from the distal end portion to the proximal end portion and to close to substantially prevent fluid from flowing through the expandable member from the proximal end portion to the distal end portion. In other specific implementations, the cover can have at least one slit near the proximal end portion to allow the cover to open.

In specific implementations, one or more of the plurality of struts can be configured to expand in a predetermined manner. In other specific implementations, one or more of the plurality of struts can have a notch at an internal face of a desired bending point to facilitate expansion of the expandable member in the predetermined manner.

In other specific implementations, some of the plurality of struts can extend from the distal end portion and some of the plurality of struts can extend from the proximal end portion. The prosthetic device can be removably coupled at a first end to the struts that extend from the distal end portion and at a second end to the struts that extend from the proximal end portion.

In another embodiment, an apparatus for delivering a prosthetic device through the vasculature of a patient comprises an elongate shaft having a distal end and a radially expandable member coupled to the distal end of the elongate shaft. The expandable member can have an open frame configuration and an outer mounting surface for mounting the prosthetic device in a collapsed state thereon. The expandable member can be configured to expand radially outwards from a first configuration to a second configuration to expand the prosthetic device.

In specific implementations, the expandable member can comprise a screw member that extends between the distal end portion and the proximal end portion, and rotation of the screw member can cause the distal end and proximal end portions to move closer together and cause the plurality of struts to expand radially.

In other specific implementations, the expandable member can comprise a plurality of longitudinally extending struts that extend between a distal end portion and a proximal end portion. In other specific implementations, one or more of the plurality of struts are configured to expand in a predetermined manner.

In other specific implementations, the expandable member can comprise a cover that at least partially surrounds the plurality of struts. The cover can be configured to open to permit fluid to flow through the expandable member from the distal end portion to the proximal end portion and to close to substantially prevent fluid from flowing through the expandable member from the proximal end portion to the distal end portion. In specific implementations, the cover has at least one slit near the proximal end portion to allow the cover to open.

In another embodiment, a method for delivering a prosthetic device through the vasculature of a patient is provided. The method can comprise providing an expandable member at a distal end of an elongate shaft, coupling the prosthetic device to the plurality of struts, and expanding the expansion device from a first configuration to a second configuration to expand the prosthetic device. The expandable member can have plurality of struts that form an open frame configuration.

In other specific implementations, the expandable member can comprise a plurality of struts that extend from a distal end portion of the expandable member to a proximal end portion of the expandable member and the method can further comprise the act of reducing the distance between the distal end portion and the proximal end portion to cause the plurality of struts to radially expand.

In other specific implementations, at least some of the plurality of struts can extend from a distal end portion of the expandable member and at least some of the plurality of struts extend from a proximal end portion of the expandable member, and the prosthetic device can be releasably coupled at a first end to the struts that extend from the distal end portion and at a second end to the struts that extend from the proximal end portion. The method can further comprise releasing the prosthetic device from the plurality of struts. In other specific implementations, after expanding the prosthetic device, the expandable member can be collapsed back to the first configuration and retracted from the body.

The foregoing and other advantages of the various embodiments disclosed herein will become more apparent from the following detailed description, which proceeds with reference to the accompanying figures.

BRIEF DESCRIPTION OF THE DRAWINGS

FIG. 21A shows a cross-sectional view of a delivery system with the anchoring device shown in FIG. 19, with the anchoring device shown in a deployed state.

DETAILED DESCRIPTION

The following description is exemplary in nature and is not intended to limit the scope, applicability, or configuration of the invention in any way. Various changes to the described embodiment may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the terms "coupled" and "associated" generally means electrically, electromagnetically, and/or physically (e.g., mechanically or chemically) coupled or linked and does not exclude the presence of intermediate elements between the coupled or associated items.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Moreover, for the sake of simplicity, the attached figures may not show the various ways (readily discernable, based on this disclosure, by one of ordinary skill in the art) in which the disclosed system, method, and apparatus can be used in combination with other systems, methods, and apparatuses. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art.

In certain embodiments, the delivery systems and methods disclosed herein can be used to deploy a frame member or stent without an expansion balloon. Thus, many of the difficulties associated with the use of such expansion balloons for delivering intraluminal devices, particularly intravascular devices, can be avoided or substantially eliminated. The delivery systems and methods disclosed herein can be substantially the same as those used in traditional methods, except that the expansion of the prosthetic devices can be achieved by effecting relative movement between mechanical elements, rather than by the expansion and contraction of a balloon member.

Figure 1:
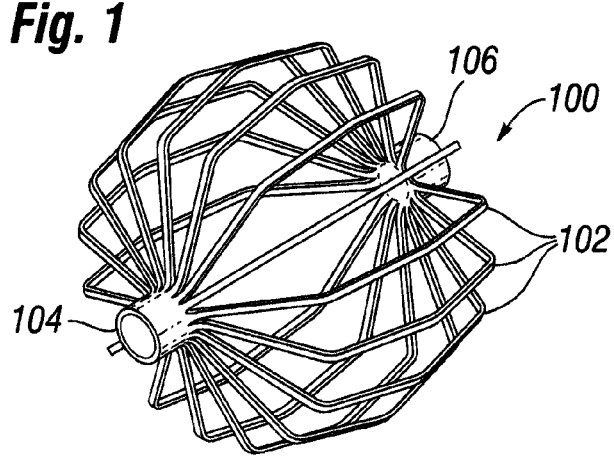
FIG. 1 is a perspective view of an expandable member for implanting a prosthetic device within the body.
Figure 2:
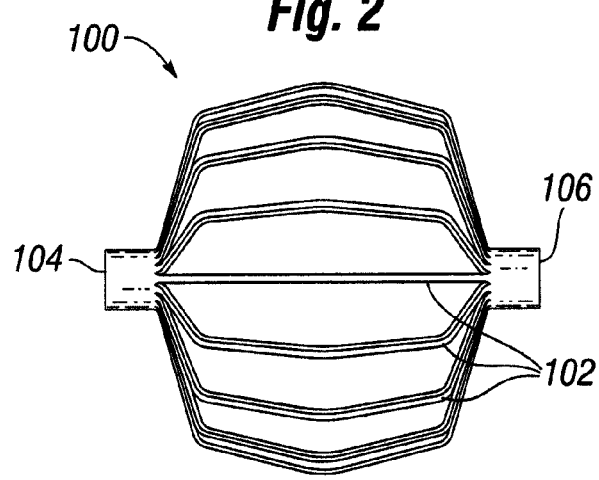
FIG. 2 is a side view of the expandable member of FIG. 1.
Figure 3:
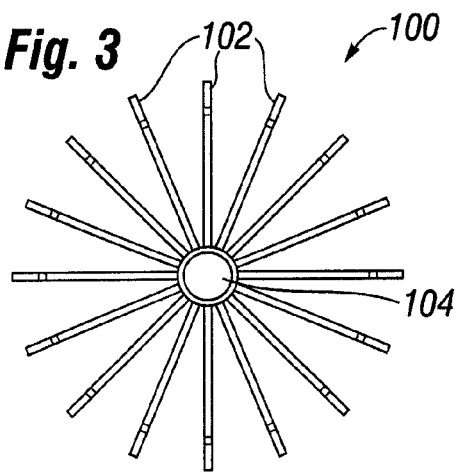
FIG. 3 is an end view of the expandable member of FIG. 1.

FIGS. 1-3 disclose an illustrated embodiment of an expandable member (expandable basket) 100 with an open-frame configuration. Expandable member 100 can comprise a plurality of longitudinally-extending, circumferentially-spaced struts 102 terminating and joined together at opposite ends of the expandable member. As shown in FIG. 1, for example, struts 102 can extend between the distal end 104 and proximal end 106 of the expandable member 100. Struts 102 can be formed of a variety of materials and in a variety of shapes, as long as the shape and structure is sufficiently strong to cause expansion of a prosthetic device, as described in more detail below. For example, each strut 102 can be formed of a tubular structure of elastic material, such as stiff plastic or metal. In addition, the expandable member 100 can be formed of a variety of number of struts 102, so long as the struts are of sufficient number, strength, and/or shape so as to provide sufficient force to surfaces and/or contact points of the prosthetic device to expand the device as described herein.

The plurality of struts 102 can define an annular supporting surface for an expandable intraluminal device to be delivered. Each strut 102 in the annular array can be laterally deformable to radially expand or radially contract the annular array of struts 102, and the annular supporting surface defined by them.

The expandable member 100 can be expandable between a first or non-expanded configuration (FIG. 5) to a second or expanded configuration (FIG. 1). The expandable member 100 is desirably configured so that shape defined by the annular supporting surface of the expandable member in its expanded configuration (FIG. 1) is substantially predetermined and known. Thus, when the expandable member 100 is expanded, the annular supporting surface of the expandable member 100 will push against the prosthetic device mounted thereon to expand the prosthetic device to a predetermined shape (i.e., a shape that is complementary to the shape of the expandable member 100 in its expanded configuration).

The expandable member 100 can be configured so that it will expand to a predetermined expanded configuration in a variety of ways. For example, struts 102 can be pre-formed or "heat-set" into a desired expanded configuration prior to deployment. The pre-formed struts 102 of perfusion basket 100 may then be stretched down or collapsed into a deployable configuration. By pre-forming struts 102 in this manner, upon expansion of the expandable member 100, the struts 102 will conform to the predetermined shape into which they have been pre-formed.

Figure 4:
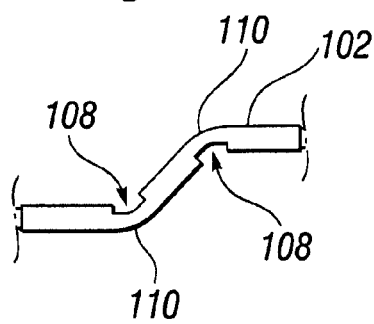
FIG. 4 is a side view of a portion of an expandable member.

Alternatively, or in addition to pre-forming struts 102, struts 102 may each include at least one notch 108 formed at an internal face of a desired bending point 110 on struts 102. Notching the appropriate bending points 110 as shown in FIG. 4, facilitates the bending of struts 102 and can provide greater control over the shape of the expandable member 100 during deployment. Also, notches 108 can allow the struts 102 to be deployed using less actuating (e.g., compressive) force. The size and depth of notches 108 can vary depending on the strength to formability ratio desired for each strut 102.

Figure 5:
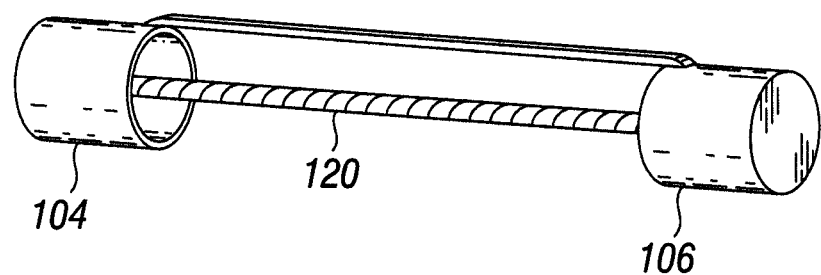
FIG. 5 is a view of an expandable member, shown in a collapsed configuration and with portions removed for clarity.
Figure 6:
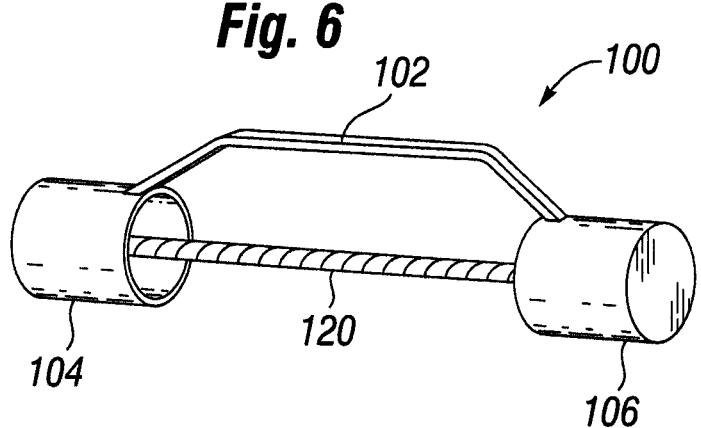
FIG. 6 is a view of an expandable member, shown in a partially collapsed configuration and with portions removed for clarity.
Figure 7:
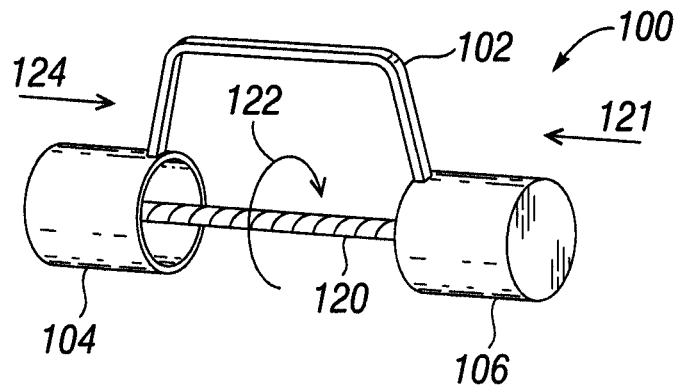
FIG. 7 is a view of an expandable member, shown in an expanded configuration and with portions removed for clarity.

A variety of different mechanisms can be used to expand and/or collapse expandable member 100. In one embodiment, as shown in FIGS. 5-7, the mechanism for expanding and/or collapsing the expandable member 100 can comprise a screw mechanism 120 configured to apply a longitudinal force to expand or collapse expandable member 100. For clarity, FIGS. 5-7 illustrate expandable member 100 with all but one strut 102 removed. Referring to FIG. 5, a prosthetic device (not shown) can be mounted on the expandable member 100 while it is in a collapsed configuration. Then the expandable member 100 can be expanded from the collapsed configuration to the expanded configuration shown in FIG. 7. FIG. 6 illustrates a partially collapsed configuration, which the expandable member 100 can pass through during expansion of the expandable member 100. Alternatively, the partially collapsed configuration (FIG. 6) can be the initial configuration of the expandable member 100. In other words, the expandable member 100 can be expandable from any first configuration (e.g., the completely collapsed configuration of FIG. 5, the partially collapsed configuration of FIG. 6, or another partially collapsed configuration) to a second, expanded configuration (e.g., FIG. 7).

Figure 8:
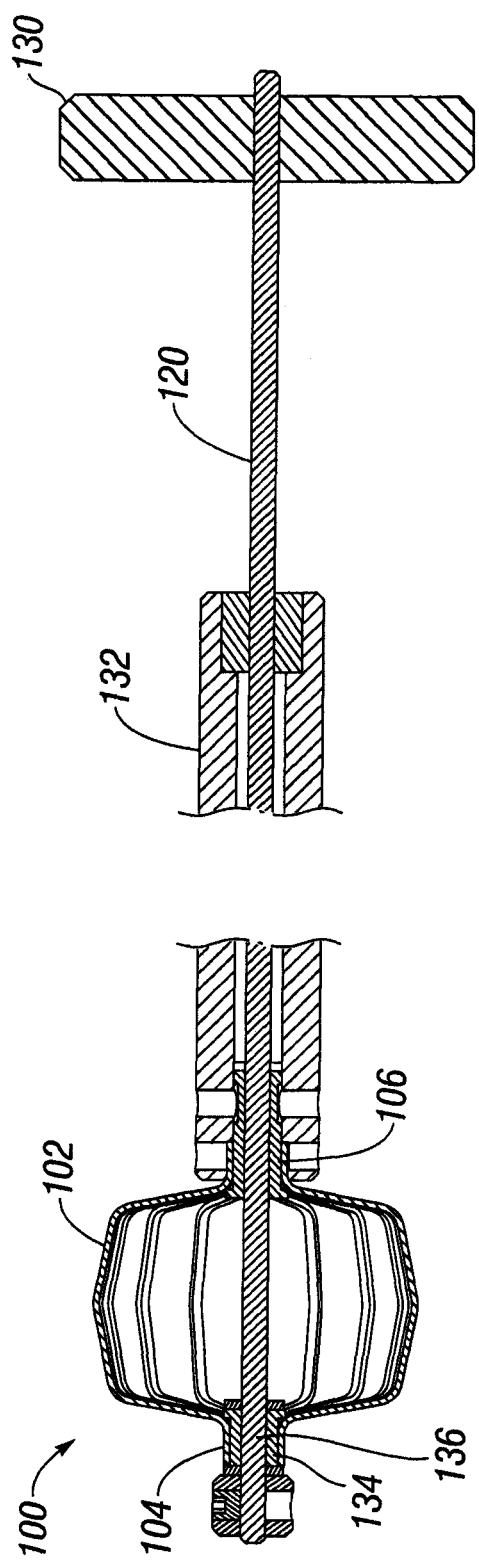
FIG. 8 is a cross-sectional view of a delivery system with an expandable member.

When in the lowest profile configuration (i.e., the initial collapsed or partially collapsed configuration), the proximal end 106 of the expandable member 100 and the distal end 104 of the expandable member are furthest apart and screw mechanism 120 is in an extended position. To expand the expandable member 100 and deploy the prosthetic device mounted thereon, the expandable member 100 can be expanded by actuating an external mechanism. Actuation of the external mechanism (for example, rotation of actuating member 130 on an external handle as shown in FIG. 8) causes screw mechanism 120 to rotate about the longitudinal axis of the expandable member 100, as shown by arrow 122 in FIG. 7. As shown in FIG. 8, screw mechanism 120 can have an externally threaded portion 136 that is received in an internally threaded portion 134 of distal end 104. The rotation of screw mechanism 120 causes the externally threaded portion 136 of screw mechanism 120 to extend further into the internally threaded portion 134 of distal end 104, causing distal end 104 to move toward proximal end 106. As the distance between the two ends of the expandable member 100 shortens, struts 102 are axially compressed (as shown by arrows 121, 124) and forced to radially expand (FIG. 7).

After the prosthetic device is expanded, the expandable member 100 can be collapsed back to a lower profile configuration for removal from the treatment site through the patient's vasculature. To return expandable member 100 to the collapsed configuration (FIG. 5) or partially collapsed configuration (FIG. 6), the rotation of screw mechanism 120 can be reversed, causing the distance between the proximal end 106 and distal end 104 of the expandable member 100 to increase and the struts to radially contract.

FIG. 8 illustrates an embodiment of a delivery system that comprises an expandable member 100 at a distal end. A rotatable actuating member 130 can be coupled to the screw mechanism 120. Screw mechanism 120 can extend longitudinally through one or more shafts 132 and attach to a distal end of expandable member 100. As discussed above, distal end 104 of expandable member 100 is preferably coupled to an internally threaded member 134 that is in threaded engagement with an externally threaded portion 136 of screw mechanism 120. Rotation of actuating member 130 causes screw mechanism 120 to rotate, shortening the distance between the proximal end 106 and distal end 104 of expandable member 100 as discussed above.

Figure 9:
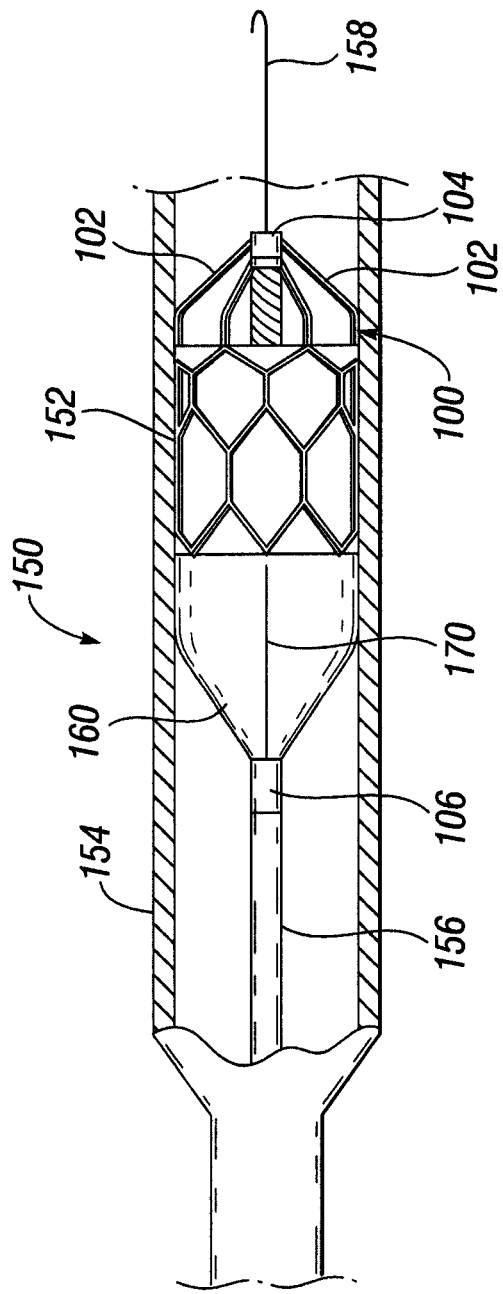
FIG. 9 is a partial cross-sectional view of a delivery system with an expandable member and a prosthetic device mounted thereon.

FIG. 9 illustrates an exemplary embodiment of a delivery system 150 for deploying a prosthetic device 152 using expandable member 100. Prosthetic device 152 can be any expandable intraluminal device, such as an expandable prosthetic heart valve. In this exemplary embodiment, delivery system 150 can include an outer member (shaft) 154 and an inner member (shaft) 156, with outer member 154 coaxially disposed around inner member 156. Outer member 154 and inner member 156 can be made from any number of suitable materials, such as a polymeric or metallic material.

Inner member 156 can comprise an expandable member 100 attached near the distal end of inner member 156. Inner member 156 can also have a guide wire lumen so that the delivery system 150 can be advanced over a guide wire 158, with the guide wire passing through the lumen. Guide wire 158 can be introduced into a body lumen and guided to the proper location in accordance with the conventional methods that used with balloon-type catheters. The expandable member 100 and prosthetic device 152 can track the guide wire 158 to the target location for deployment of the prosthetic device 152.

FIG. 9 shows struts 102 of the expandable member 100 in a substantially unexpanded configuration. FIG. 9 illustrates the expandable member 100 in a partially collapsed configuration (as shown in FIG. 6); however, as discussed above, expandable member 100 could be further collapsed (as shown in FIG. 5) to achieve a lower profile configuration. Prosthetic device 152 is shown mounted on the outer surfaces of struts 102, which collectively define an annular surface for receiving prosthetic device 152 in a contracted state. As shown in FIG. 9, expandable member 100 can be collapsed into and constrained by the distal end of outer member 154, which forms a sheath extending over the valve. Thus, prosthetic device 152 can be constrained and/or positioned in a contracted condition between outer member 154 and the annular surface defined by struts 102. Prosthetic device 152 can be maneuvered through the patient's vasculature to the treatment site while mounted on expandable member 100, as shown in FIG. 9.

Alternatively, as described in U.S. Patent Publication No. 2008/0065011 and U.S. patent application Ser. No. 12/247,846, the prosthetic device 152 can be initially mounted in a collapsed (crimped) state at a location that is either distal or proximal to expandable member 100. The entire disclosures of U.S. Patent Publication No. 2008/0065011 and U.S. patent application Ser. No. 12/247,846 are incorporated by reference herein. After the prosthetic device is advanced through narrow portions of the patient's vasculature (for example, the iliac artery which is typically the narrowest portion of the relevant vasculature), the prosthetic device can be positioned on (or over) the expandable member 100. If the prosthetic device has not yet been advanced to the deployment site when the expandable member is repositioned underneath the prosthetic device, then the prosthetic device and expandable member can be advanced to the treatment site together and the expandable member can be expanded to deploy the prosthetic device at the treatment site. In this manner, prosthetic device can be crimped to an even smaller diameter and the profile of the delivery system can be further reduced.

Figure 10:
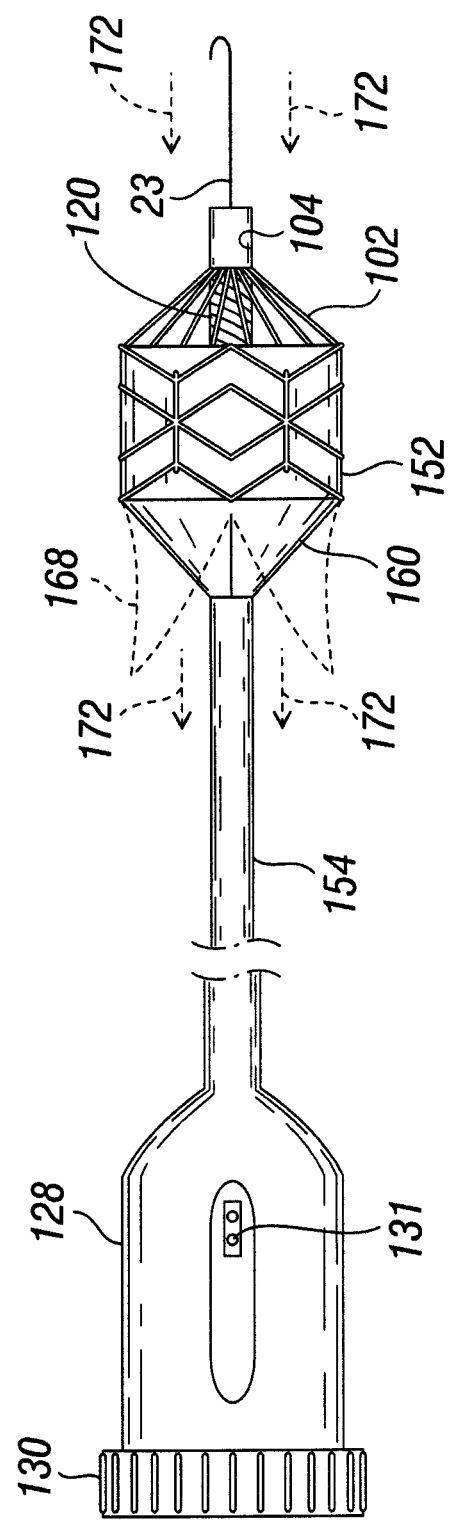
FIG. 10 is a view of a delivery system with an expandable member and a prosthetic device mounted thereon, shown with a cover and with the expandable member in an expanded configuration.

Once the prosthetic device 152 and expandable member 100 reach the desired deployment location, outer member 154 can be retracted proximally, exposing the prosthetic device 152 for deployment. FIG. 10 illustrates the expandable member 100 in an expanded configuration after the outer member 154 has been retracted relative to the expandable member 100. The expansion of expandable member can be caused (as discussed above) by actuating screw mechanism 120 to compress the expandable member 100 longitudinally and force struts 102 to expand radially. As shown in FIG. 10, the delivery system can have an actuating member 130 positioned on or around an external handle member 128. External handle member 128 can have visual indicia 131 which indicate the amount of expansion of expandable member. The rotation of the actuating member 130 (as discussed above, for example, with regard to FIG. 8) forces struts 102 on expandable member 100 to longitudinally contract and radially expand, causing prosthetic device 152 to be expanded and anchored at the target location.

Figure 11:
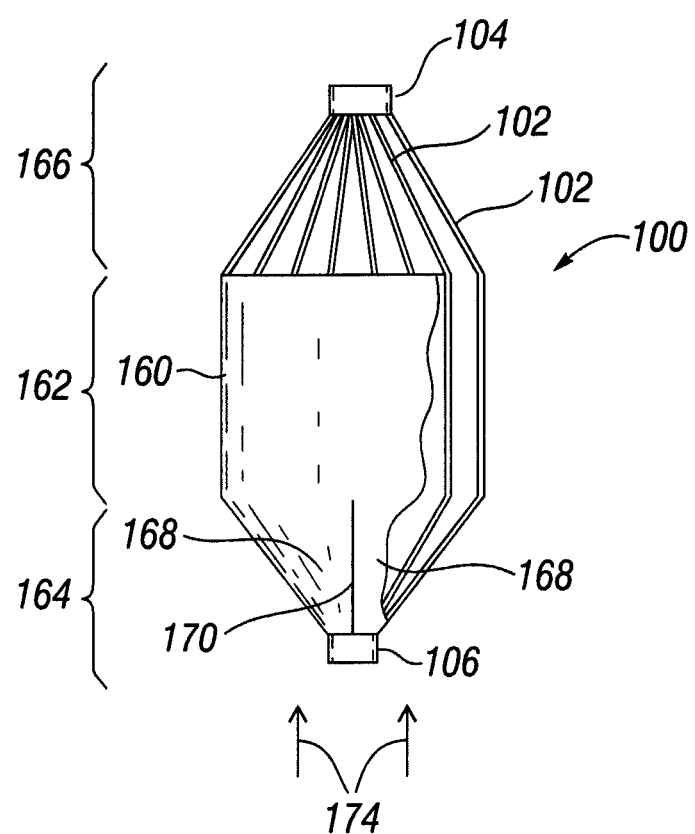
FIG. 11 is a partial cross-sectional view of an expandable member with a cover at least partially surrounding the expandable member.
Figure 12:
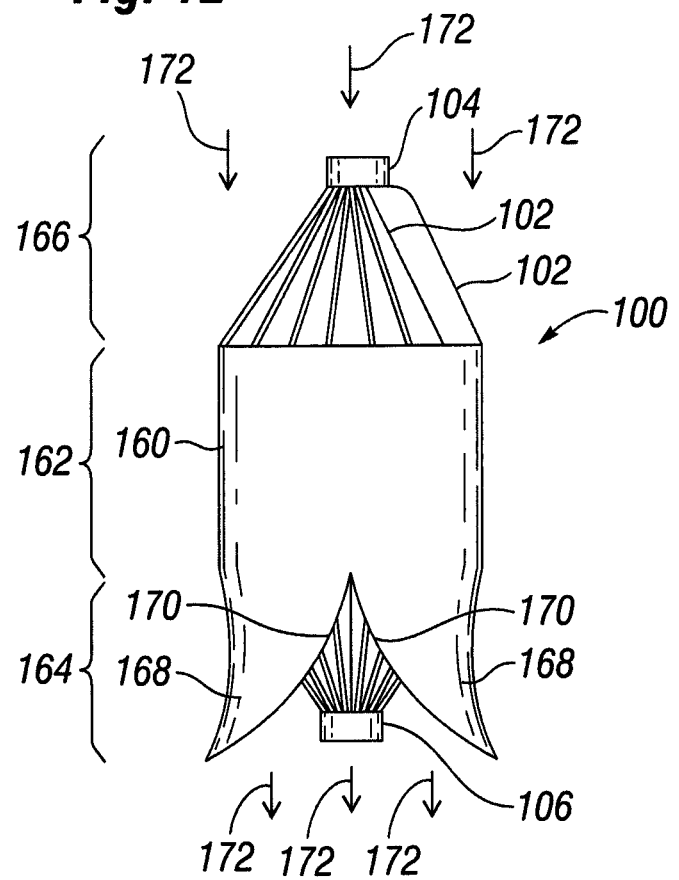
FIG. 12 is a view of an expandable member with a cover at least partially surrounding the expandable member, with the cover shown in an open configuration.

The delivery system 150 shown in FIGS. 9 and 10 desirably also comprises a cover 160 that at least partially surrounds expandable member 100. As shown in FIGS. 11 and 12, cover 160 can be disposed over a working length (prosthetic device mounting area) 162 of the expandable member 100, with cover 160 extending the length of prosthetic device 152 and over a proximal end portion 164 of expandable member 100. For clarity, FIG. 11 shows cover 160 partially cut-away, showing the location of struts 102 beneath cover 160 at the working length 162 and proximal end portion 164. Desirably, distal end portion 166 remains uncovered as shown in FIG. 11. Cover 160 is desirably attached to the outer surface of struts 102 along the working length 162. Cover 160 is desirably includes one or more slits 170 and is at least partially detached from the outer surface of struts 102 at proximal end portion 164.

Slits 170 can be arranged approximately 120 degrees about the circumference of cover 160 at proximal end portion 164. Slits 170 allow proximal end portion 164 of cover 160 to act as temporary leaflets 168, which may open (second configuration) when fluid flows through expandable member 100 from the distal end 104 to the proximal end 106 as indicated by arrows 172 (FIGS. 10 and 12) and close (first configuration) as when fluid tries to pass through expandable member 100 from the proximal end 106 to the distal end 104 as indicated by arrows 174 (FIG. 11).

By providing a cover 160 that permits fluid flow in one direction, but restricts it in the other, the delivery system can mimic a native valve while the prosthetic device 152 is being deployed. In conventional systems, for example, a balloon member can occlude the orifice (such as the aortic valve) causing difficulties. The pressure drop across the aortic valve when the valve is closed and the flow across the valve (~5 L/min) is so great that occlusion of the annulus may result in the ventricle ejecting the occluding member (e.g., expandable balloon) into the aorta. By permitting flow through the expandable member, pressure build-up during prosthetic device deployment can be avoided.

Also, by allowing fluid to flow through the orifice during deployment of the prosthetic device, the need for pacing the heart can be reduced or entirely eliminated. Although current pacing procedures are effective, they still require rapid deployment of prosthetic devices. For example, in certain procedures, the prosthetic device should be deployed in about 3 to 5 seconds. Since the deployment systems described herein permit flow across the orifice during deployment of the prosthetic device, the prosthetic device can be deployed more slowly, and can be repositioned and/or moved by an operator during deployment. In contrast, pacing procedure do not generally allow for any repositioning or movement of the prosthetic device during deployment. Additionally, by eliminating pacing, the procedure can be greatly simplified and variations in patient anatomy and systems (e.g., ventricular pressure and flow) for the purpose of pacing need not be considered.

Figure 13:
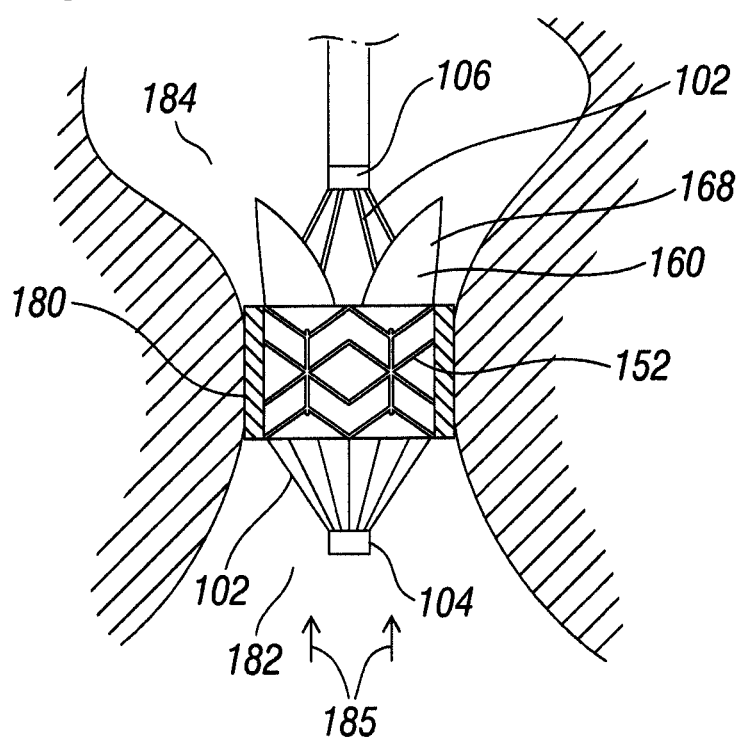
FIG. 13 is a partial cross-sectional view of a prosthetic device being expanded within the body by an expandable member.

FIG. 13 illustrates a specific embodiment where the prosthetic device 152 is a prosthetic heart valve that is to replace the native aortic valve. The embodiments disclosed herein permit blood to flow from the left ventricle 182 through the expandable member 100 and into the aorta 184. As the prosthetic device 152 is moved into position at the aortic annulus 180, blood can flow from the left ventricle 182 through the aortic annulus 180 into the aorta 184 (as shown by arrow 185). However, when the flow of blood is reversed, cover 160 closes (as shown in FIG. 11) and at least substantially blocks blood from flowing from the aorta 184 back into the left ventricle 182. Thus, while prosthetic device 152 is being deployed cover 160 (and its leaflets 168) open (as shown in FIGS. 10, 13, and 13) allowing blood to flow into the aorta. When the ventricles finish contracting and begin to relax, however, cover 160 (and its leaflets 168) move against struts 102 at the proximal end portion 164 (FIG. 11) and substantially prevent blood from flowing back into the left ventricle.

Cover 160 can also provide protection to flexible membranes or other components of the expandable prosthetic device to be delivered by forming a barrier between struts 102 and the prosthetic device during delivery and deployment of the prosthetic device at the treatment site. Cover 160 can be formed of any suitable material, including, for example urethane and the like. Moreover, instead of the slits 170 and leaflets 168 shown in the illustrated embodiments, cover 160 can comprise any suitable shape and configuration, so long as that shape and configuration is suitable to restrict flow in one direction and permit flow in the other direction during placement and deployment of the prosthetic device.

Various prosthetic devices are suitable for deployment with the delivery systems disclosed herein, including, for example, heart valves that comprise expandable frame members and one or more leaflet members attached to the expandable frame members. After deployment of the prosthetic device, the expandable member can be radially contracted as discussed above and the expandable member can be retracted from the body.

Figure 14:
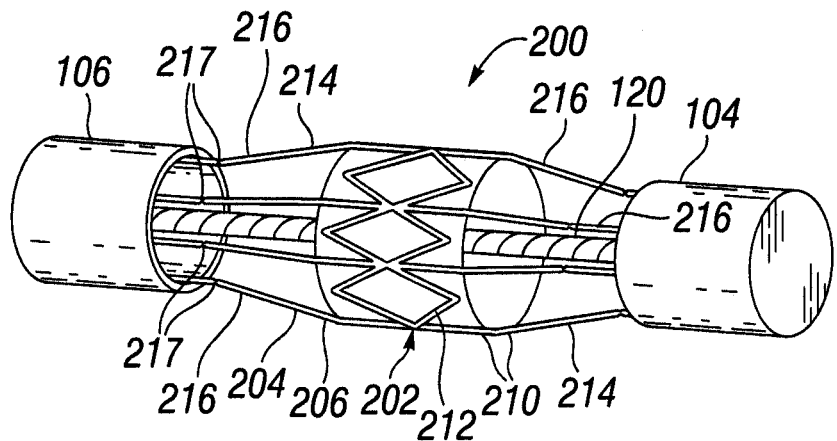
FIG. 14 is a view of a delivery system with an expandable member, shown with a prosthetic device mounted thereon.
Figure 15:
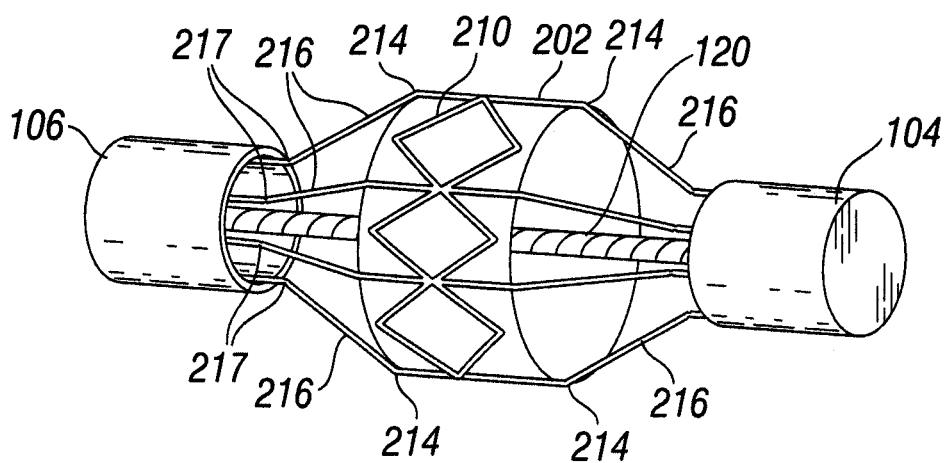
FIG. 15 is a view of a delivery system with an expandable member and prosthetic device mounted there, shown in an expanded configuration.

In other embodiments, the prosthetic device itself can comprise at least a portion of the expandable member. FIG. 14 is an illustration of a delivery system 200 where the open-frame expandable member comprises a prosthetic device. In the illustrated embodiment, delivery system 200 comprises an implantable prosthetic device 202 (hereinafter "valve 202") that is suitable for percutaneous deployment and that is releasably coupled to expansion struts 216 to form an expandable member. Valve 202 is preferably adapted to be radially crimped and radially expanded, which simplifies navigation through the narrow passages of the patient's vasculature during delivery and positioning of valve 202. Valve 202 preferably also comprises a flexible membrane 204 and a collapsible support structure (frame) 206.

After deployment at a treatment location, flexible membrane 204 can be positioned in a flow path through valve 202 to permit flow in a first direction, and substantially resist flow in a second direction. In one embodiment, flexible membrane 204 can include a collapsible pliant material formed as flexible leaflets 208, which can be arranged to collapse in, for example, a mono cusp, bicuspid, or tricuspid arrangement.

In the illustrated embodiment, collapsible support structure 206 can be expandable from a first diameter to a second diameter, and can have a flow path through the collapsible support structure 206 along its structural axis. Collapsible support structure 206 can include a generally cylindrical expandable framework of frame members 210, which primarily secure valve 202 at or adjacent to the defective valve annulus. Collapsible support structure 206 can provide stability to the valve 202 and help to prevent valve 202 from migrating after it has been implanted.

Prosthetic valves of this type are usually implanted in one of the channels of the body to replace a native valve. In the illustrated embodiment, the prosthetic valve will be explained in connection with a cardiac valve prosthesis configured for implantation at the aortic annulus; however, it should be understood that the delivery systems disclosed herein can be used with other expandable members and prosthetic devices.

Collapsible support structure 206 may be a support stent configured to crimp evenly so as to present a relatively low profile or narrow configuration. The collapsible support structure 206 can also be radially deployable from the low profile configuration so as to extend to occupy the passage at the target location for implantation in a body duct. In one embodiment, collapsible support structure 206 can comprise a series of frame members (struts) 210 arranged and connected to define a geometrical structure that causes collapsible support structure 206 to expand radially as the structure is compressed axially. For example, frame members 210 can define substantially diamond shaped cells 212 that when axially compressed force collapsible support structure 206 to expand radially. Valve 202 can be releasably coupled to connecting struts (linkages) 216 at attachment areas 214 located at proximal and distal ends of valve 202.

In operation, a delivery catheter advances valve 202 while coupled to expansion struts 216 through a sheath over a guidewire to a target location in a body duct, for example, the aortic valve. As shown in FIG. 14, when in a collapsed position, connecting struts 216 can be disposed substantially axially relative to the deployment system. To expand valve 202, the distance between distal end 104 and proximal end 106 can be shortened by rotating screw mechanism 120. As discussed above, the rotation of screw mechanism causes distal end 104 to move closer to proximal end 106, which forces connecting struts 216 to extend radially. To facilitate the radial expansion of connecting struts 216, the connecting struts can have hinge or bend areas 217, about which the connecting struts bend. These bend areas can be pre-formed or notched, or otherwise configured so that connecting struts 216 will radially extend at the bend area 217 when they are axially compressed.

Figure 16:
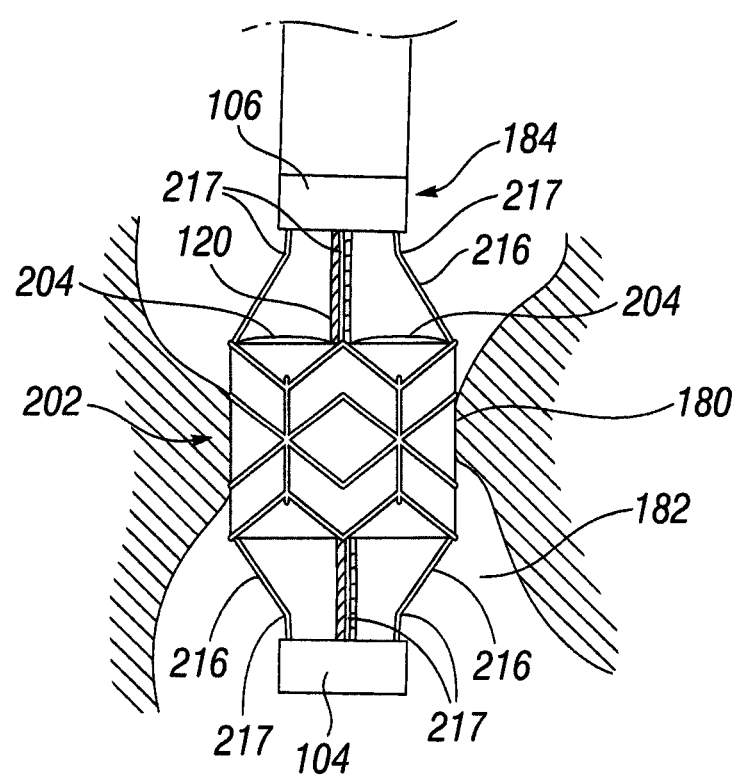
FIG. 16 is a view of a delivery system with an expandable member at a treatment site in the body, with a prosthetic device shown in an expanded configuration.

Because connecting struts 216 are connected to frame members 210 at attachment areas 214, the radial expansion of connecting struts 216 applies radially directed forces to the valve 202 via frame members 210. The radially movement of connecting struts 216 causes valve 202 to radially expand (deploy). As shown in FIG. 16, once valve 202 begins to expand, leaflets 204 may be immediately activated and begin to regulate flow through the annulus. Once valve 202 is completely deployed, connecting struts 216 may be disengaged from attachment areas 214 and removed from the target location.

Figure 17A:
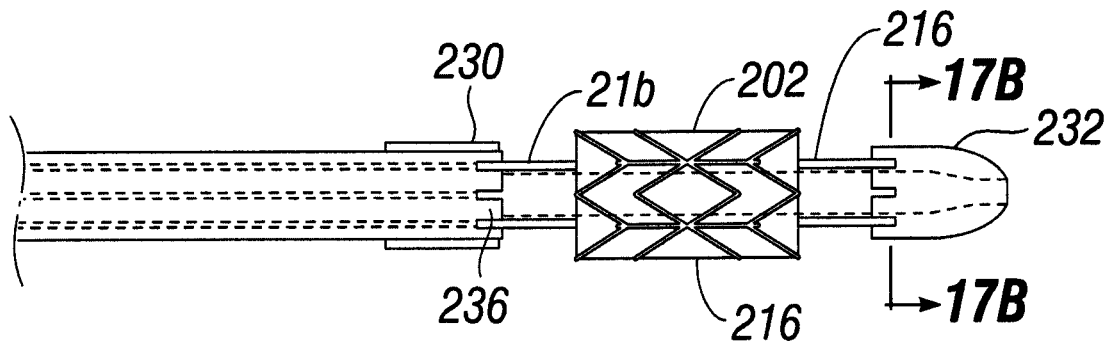
FIG. 17A is a delivery system with an expandable member and a collapsed prosthetic device mounted thereon.
Figure 17B:
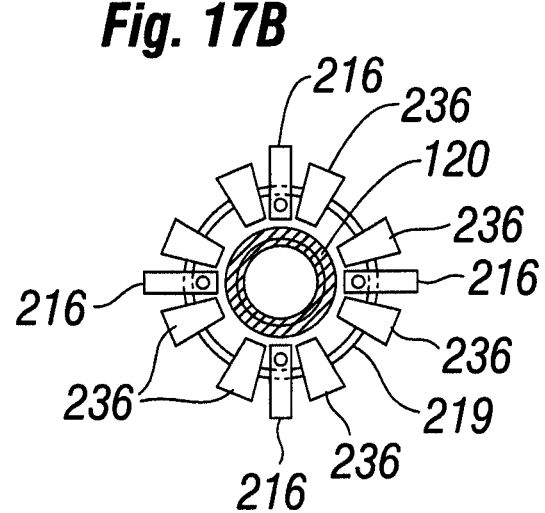
FIG. 17B is a cross-sectional view taken at line 17B-17B of FIG. 17A.
Figure 18:
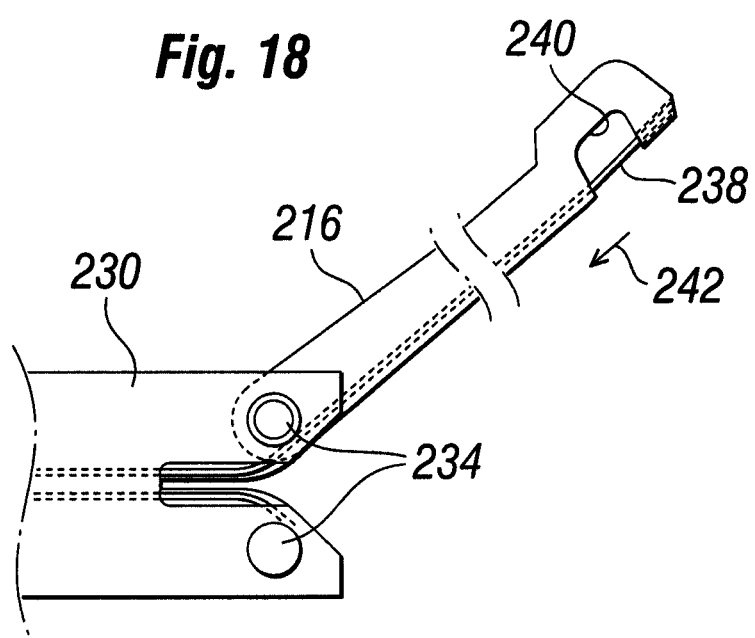
FIG. 18 is a view of a strut of an expandable members and a connection means for connecting the strut to a prosthetic device.

In a specific implementation shown in FIGS. 17A, 17B, and 18, connecting struts 216 can be pivotably coupled to a portion of annular members 230, 232 at pivot connection areas (bending areas) 234. For example, in one embodiment, the proximally located connecting struts can be coupled to a first annular member 230 at the proximal end and distally located connecting struts can be coupled to a second annular member 232 at the distal end. Annular members 230 and 232 can comprise a plurality of adjacent, circumferentially spaced extending members 236 with spaces located between adjacent extending members 236 for receiving connecting struts 216. Connecting struts 216 can be positioned and captured between extending members 236 and configured to pivot or bend about pivot connection area 234. A ring member 219 can pass through each of the connecting struts 216 to hold each connecting strut 216 in position at one of the annular members 230 and 232.

In this and in the other embodiments, the number of connecting struts 216 can vary. For example, FIG. 17B illustrates four circumferentially spaced connecting struts 216; however, more or fewer connecting struts 216 can be used, so long as the outwardly directed force generated by the connecting struts 216 as they undergo compression is sufficient to expand valve 202 from an unexpanded configuration with a smaller diameter to an expanded configuration with a greater diameter. In the illustrated embodiment, FIG. 17B shows eight different locations between extending members 236 into which connecting struts 216 can be located.

Relative movement of annular members 230 and 232 can be caused by a screw mechanism or other axially applied forces (as described in more detail above), causing connecting struts 216 to expand radially. To expand valve 202 uniformly, it can be desirable to space connecting struts 216 annularly around annular members 230 and 232. In addition, it may be desirable to connect struts 216 to the valve at areas where the valve has structural supports or posts so that the valve has sufficient rigidity at the area where struts 216 contact valve 202.

Various means for attaching connecting struts 216 to valve 202 can be used. For example, connecting struts 216 can have a first end pivotably coupled to annular members 230 and 232, and a second end that comprises a securing mechanism for securing the valve 202 to the connecting strut as shown in FIG. 18. For example a wire member 238 can pass through connecting strut 216 and a portion of the valve 202 can be captured between wire 238 and a holding area 240 of connecting strut 216 (e.g., wire member 238 can pass through a loop or opening formed in one of struts 210 and positioned in area 240). The valve 202 can be released from connecting strut 216 by pulling wire 238 towards a proximal end (in the direction of arrow 242) a distance great enough to release valve 202 from the holding area 240.

Figure 19:
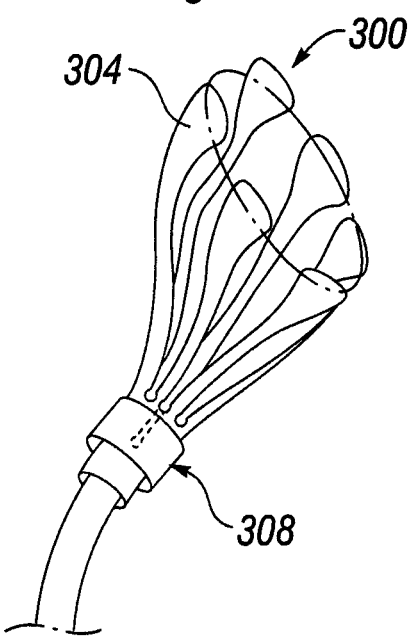
FIG. 19 shows a view of an anchoring device.
Figure 20:
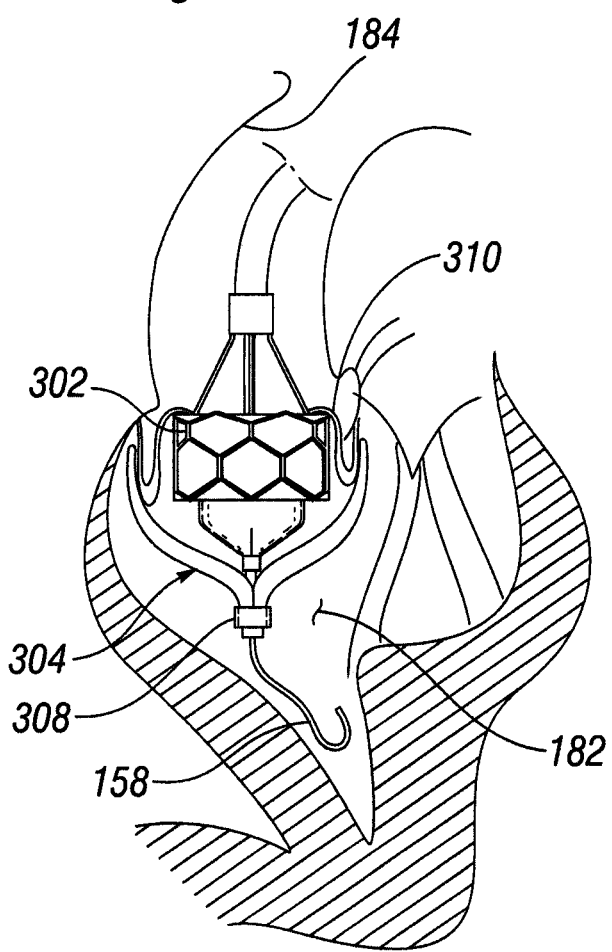
FIG. 20 shows a view of the anchoring device of FIG. 19 positioned within the body to hold a prosthetic device in position relative to the anchoring device.

FIGS. 19-21 show an embodiment of an expandable anchoring device 300 that can be used to hold a valve 302 in a desired position during deployment of valve 302. As shown in FIG. 19, anchoring device 300 can include a plurality of flexible members, or fingers, 304. These flexible members 304 can be used to anchor the delivery system in place during deployment of valve 302. As shown in FIG. 20, for example, during deployment of a prosthetic device (valve 302) at an aortic annulus, flexible members 304 can be expanded in the left ventricle, where flexible members 304 can be configured to contact a portion of tissue surrounding the native aortic valve 310. Once deployed, anchoring device 300 can fix the position of valve 302 relative to the native valve 310. Thus, valve 302 can then be expanded in the native valve 310 without concern for positioning error caused by, for example, movement of the beating heart or the blood pressure through the native valve 310.

In addition, anchoring device 300 can help hold the valve in the proper position by preventing the delivery system from moving proximally during deployment. For example, after expansion of anchoring device 300 within the left ventricle, the delivery system can be moved proximally until the anchoring device 300 contacts the ventricle walls near the aortic annulus, effectively preventing the delivery system from moving any further proximally. After the anchoring device 300 secures the relative position of the prosthetic device (valve), the prosthetic device can be expanded at the aortic annulus.

Figure 21A:
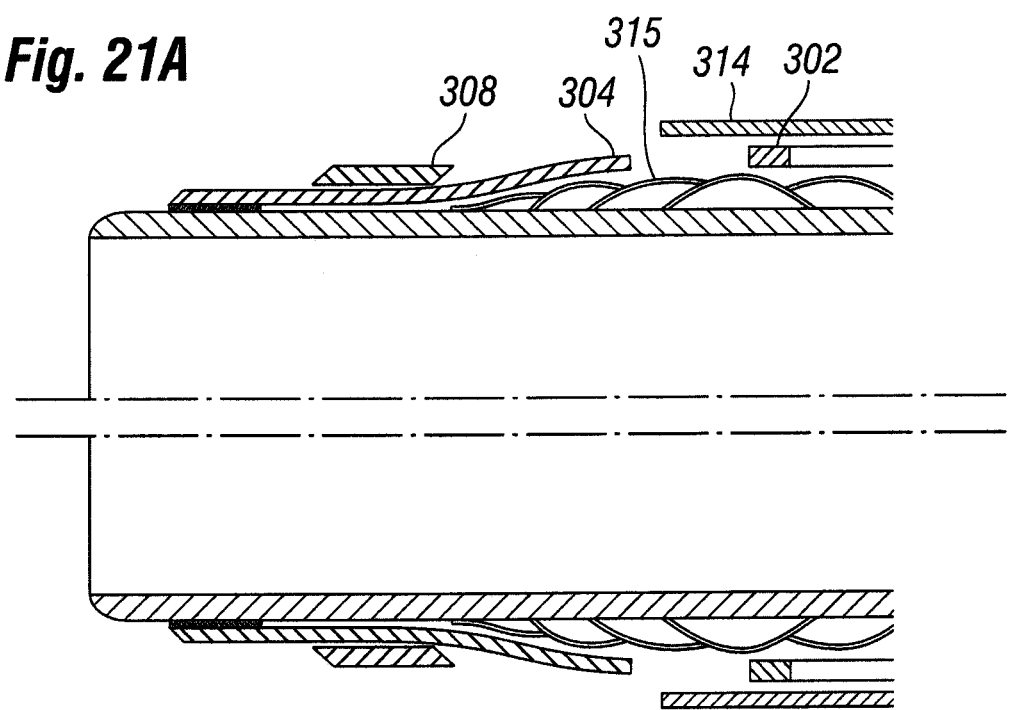
FIG. 21A shows a cross-sectional view of a delivery system with the anchoring device shown in FIG. 19, with the anchoring device shown in a non-deployed state.
Figure 21B:
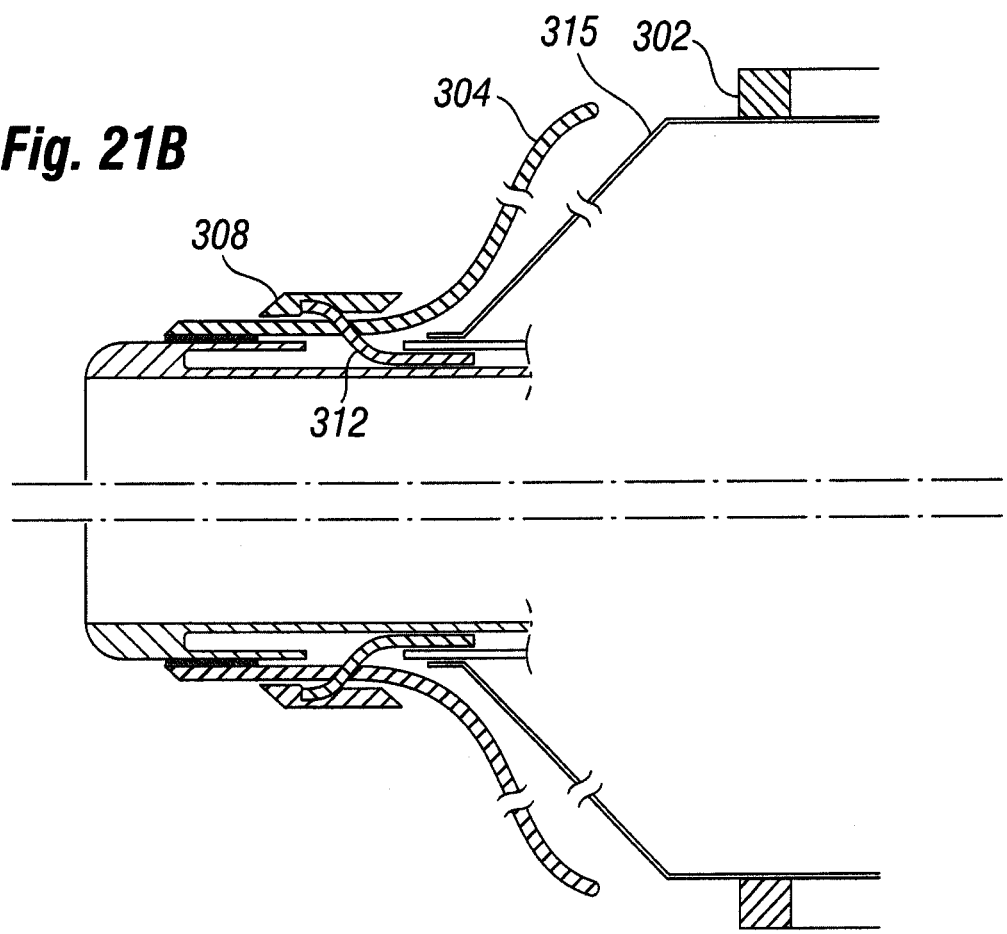

Referring to FIGS. 21A and 21B, the anchoring device 300 can be delivered to the treatment site (or anchoring location) constrained in an outer member (cover) 314. To deploy anchoring device 300, outer member 314 can be retracted, exposing flexible members 304. Flexible members 304 can be biased outwards and upon retraction of the cover member 314, flexible members 304 radially expand and can be placed in contact with tissue near the native annulus 310. The expandable portion of the anchoring device can be formed in a variety of shapes. For example, if desired, flexible members 304 can be replaced with an expandable braided cup. After positioned appropriately, valve 302 can be expanded using a member 315, which can be, for example, an expandable member as described herein or a balloon member.

To remove anchoring device 300 from the treatment location, a retraction collar 308 can be utilized to "recapture" flexible members 304. In one embodiment, a pull wire 312 can be attached to a collar 308 that is located near the distal ends of flexible members 304 of anchoring device 300. By pulling pull wire 312 proximally, the collar 308 can move proximally over flexible members 304, causing them to radially collapse along the axis of the delivery system. Once collapsed, the anchoring device 300 can be removed from the treatment site by being retracted from the body through a catheter of the delivery system.

Figure 22:
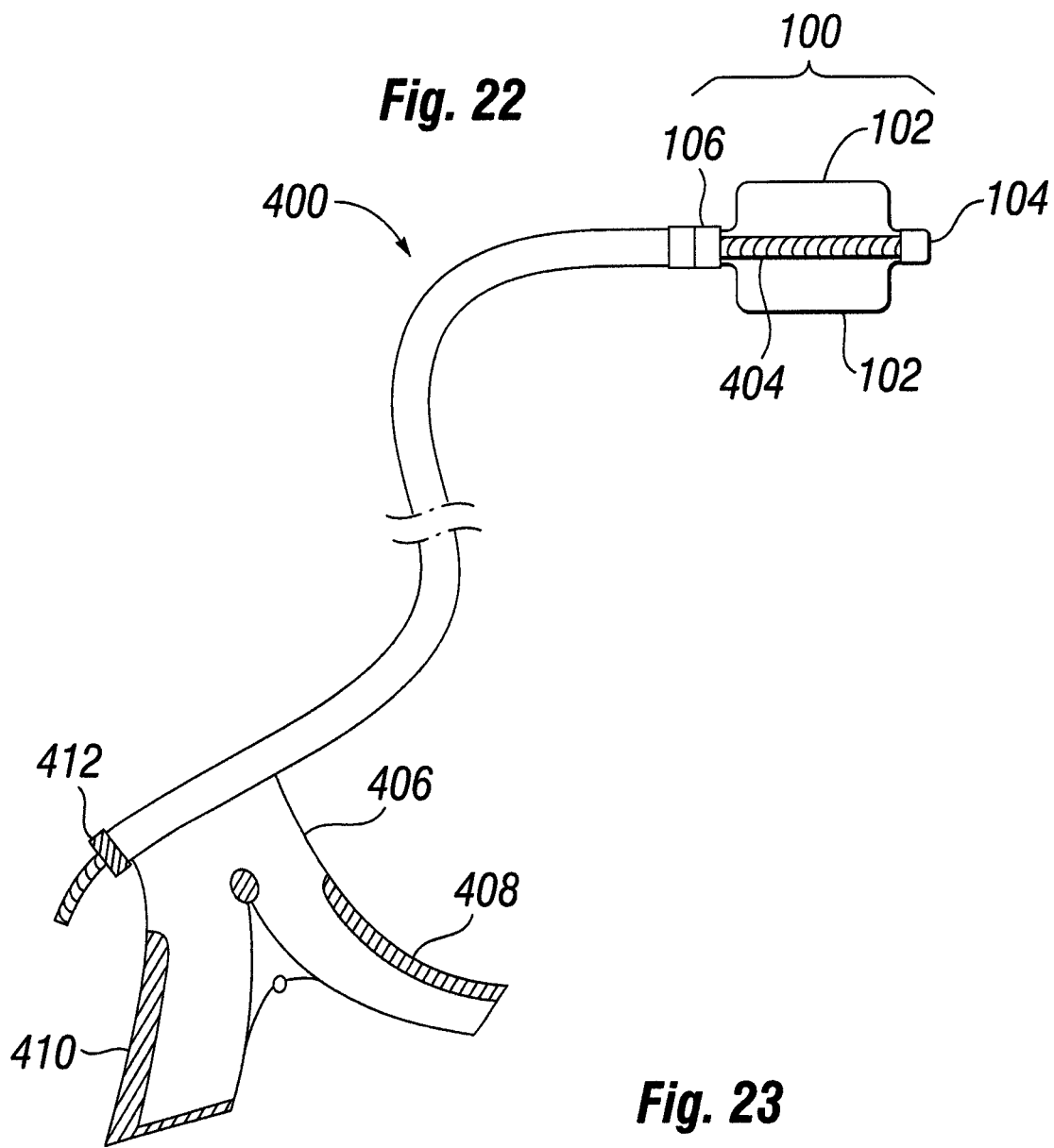
FIG. 22 shows an illustration of a delivery system that has an expandable member that is deployable by a ratchet mechanism.

Screw mechanism 120 is a particularly desirable mechanism for expanding the expandable member, since it can provide significant compressive force at a local area (e.g., the expandable member), thereby forcing the expandable member to radially expand without imparting significant forces throughout other locations of the delivery system. However, as discussed above, other mechanisms for expanding the expandable member can be utilized. For example, FIG. 22 illustrates another embodiment of a deployment system where the distance between the distal end 104 and proximal end 106 of an expandable member 100 can be adjusted to expand a valve or other prosthetic device.

In this embodiment, the distance between the two ends of the expandable member can be adjusted by applying a longitudinal (non-rotational) force the length of the deployment system 400. As with the other deployment systems described herein, deployment system 400 can be used for delivering a prosthetic device, such as a heart valve, but is not limited thereto, and may be adapted to stent delivery systems as well. In one embodiment, deployment system 400 can include a shaft 402 that can track through the vasculature and yet have sufficient "longitudinal" compressive strength to allow a wire or cable 404 to be pulled through a center lumen defined through shaft 402 with sufficient force to deploy, for example, expandable member 100 (shown with some struts 102 removed for clarity).

Figure 24:
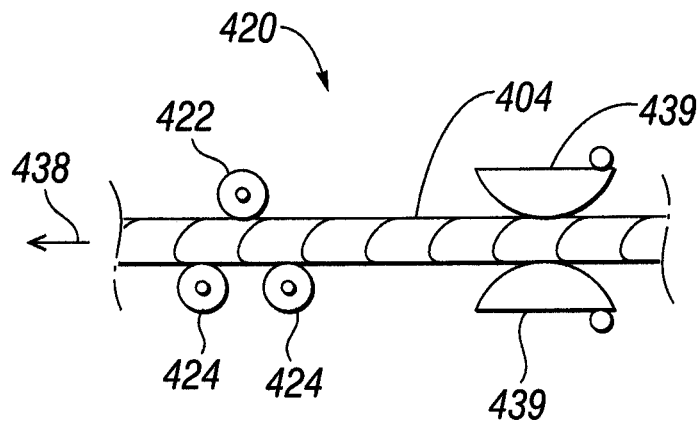
FIG. 24 shows an illustration of a mechanism for use with a delivery system of the type shown in FIG. 22.

In one embodiment, one end of wire 404 extends through expandable member 100 and is coupled to distal end 104 of expandable member 100. A proximal end of wire 404 is operatively coupled to a handle 406 to interface with a ratcheting mechanism 420 (shown in FIG. 24).

Ratcheting mechanism 420 may be activated, for example, by gripping and squeezing handles 408 and 410 (FIG. 22) to cause wire 404 to be pulled proximally through the center lumen of shaft 402 and locked into place by opposing locking wheels 422, 424 (FIG. 24) in a manner well known by those of ordinary skill in the art. Other locking elements 439 can be provided to at least temporary secure the position of wire 404 relative to shaft 402. A release knob 412 may also be included on handle 406 and used to release locking wheels 422, 424 and the tension on wire 404 as desired.

Figure 23:
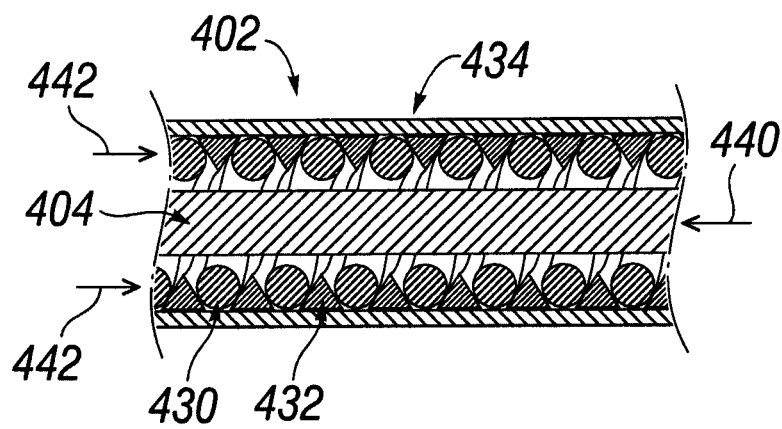
FIG. 23 shows an illustration of a shaft suitable for use with the delivery system of FIG. 22.

FIG. 23 is a cross sectional view along the longitudinal length of flexible shaft 402. In one embodiment, flexible shaft 402 is composed of a circular cross section closed wound coil 430 interposed with a triangular cross section closed wound coil 432. Each coil 430 and 432 is confined within a tubular cover 434, which can be made of vinyl or a similar material. Coils 430 and 432 define a lumen extending the length of flexible shaft 402 with wire 404 disposed therein.

In operation, once expandable member 100 is positioned as desired in the vasculature, ratcheting mechanism 420 of handle 406 can be activated. Ratcheting mechanism 420 pulls proximally (in the direction of arrow 438) on wire 404, this in turn, pulls distal end 104 of expandable member 100 toward proximal end 106 to cause expandable member 100 to "deploy" in a manner previously described. The resulting force (shown by arrow 440) used to pull on wire 404 is transferred to shaft 402, which is configured to absorb the compressive load and resist compression (shown by arrow 442) without significant buckling or shape distortion of shaft 402.

Since shaft 402 provides a stable mounting platform, in an alternative embodiment, instead of deploying expandable member 100 by pulling on wire 404, a rotation actuator 450 can be used. Advantageously, since rotation actuator 450 is mounted to a "rigid" platform, the twisting actuation is acceptable.

Figure 25:
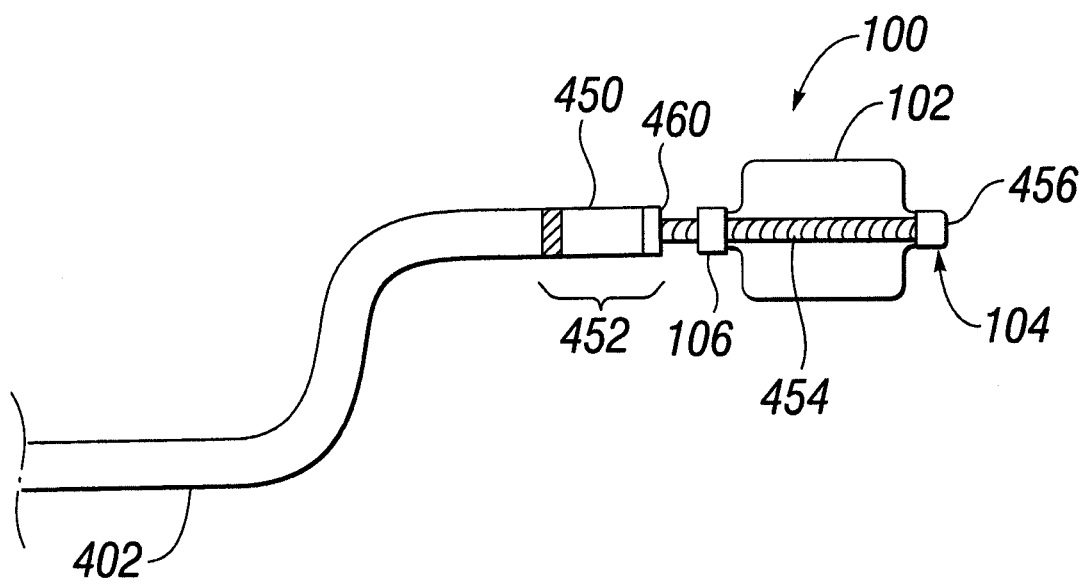
FIG. 25 shows an illustration of a delivery system with an expandable member that is operable using an actuation device positioned adjacent the expandable member.

The mechanisms described herein can also be actuated by a variety of power sources. For example, the screw mechanisms described above can be actuated using a power source such as a motor or battery. In the illustrated embodiment shown in FIG. 25, a rotation actuator 450, such as DC motor or equivalent, is coupled to the distal end 452 of shaft 402. In this embodiment, rotation actuator 450 may be coupled to a drive shaft 454, such as a threaded rod. Drive shaft 454 can be operatively engaged with a threaded receptacle 456 positioned on a distal end 104 of expandable member 100 (some struts 102 removed). Operationally, rotation actuator 450 makes drive shaft 454 rotate causing threaded receptacle 456 to traverse linearly upon drive shaft 454. The linear movement of threaded receptacle 456 toward proximal end 106 causes distal end 104 to move toward proximal end 106 to deploy expandable member 100.

In one embodiment, a gear reduction mechanism 460 can be added to rotation actuator 450 to create a higher output torque and also allow for fine tuning of the placement procedure. It should be understood that variations in motor voltage (DC only), gearbox ratios, and screw thread pitch may be used to obtain the required or desired torque needed to deploy expandable member 100.

The apparatuses and methods described herein can improve what currently is one of the most critical stages of the deployment procedure by allowing a physician to more accurately position and deploy a prosthetic device without disrupting patient hemodynamics.

Although the specific embodiments discussed above describe methods and apparatuses for expanding various prosthetic devices, it should be understood that the devices and methods disclosed herein can be used for other purposes. For example, the expandable members disclosed herein can be used to replace expandable balloon members in a variety of medical procedures. Thus, the expandable members described herein can be used, for example, for angioplasty (e.g., opening clogged coronary arteries), valvuloplasty (e.g., dilating a stenotic heart valve), and other procedures in which expanding balloon members are conventionally utilized.

The invention has been disclosed in an illustrative manner. Accordingly, the terminology employed throughout should be read in an exemplary rather than a limiting manner. Although minor modifications of the invention will occur to those of ordinary skill in the art, it shall be understood that what is intended to be circumscribed within the scope of the patent warranted hereon are all such embodiments that reasonably fall within the scope of the advancement to the art hereby contributed, and that scope shall not be restricted, except in light of the appended claims and their equivalents.

We claim:

1. An apparatus for delivering a prosthetic device through the vasculature of a patient comprising:
    an elongate shaft having a distal end;
    a radially expandable member coupled to the distal end of the elongate shaft, the expandable member comprising a distal end portion and a proximal end portion that are movable relative to one another between a first orientation and a second orientation; and
    a plurality of struts coupled to at least one of the distal end and proximal end portions and having a prosthetic device receiving area,
    wherein in the first orientation the distal end and proximal end portions are a first distance apart, and in the second configuration the distal end and proximal end portions are a second distance apart, the second distance being less than the first distance, and
    wherein movement of the distal end and proximal end portions from the first orientation to the second orientation causes connecting members to expand radially outwards from a first configuration to a second configuration to expand the prosthetic device,
    wherein one or more of the plurality of struts extend from the distal end portion to the proximal end portion,
    wherein the expandable member comprises a cover that at least partially surrounds the plurality of struts, and
    wherein the cover is configured to open to permit fluid to flow through the expandable member from the distal end portion to the proximal end portion and to close to substantially prevent fluid from flowing through the expandable member from the proximal end portion to the distal end portion.

2. The apparatus of claim 1, wherein the expandable member comprises a screw member that extends between the distal end portion and the proximal end portion, and rotation of the screw member causes the distal end and proximal end portions to move from the first to the second orientation.

3. The apparatus of claim 1, wherein the expandable member comprises a wire that extends between the distal end portion and the proximal end portion, and movement of the wire causes the distal end and proximal end portions to move from the first to the second orientation.

4. The apparatus of claim 1, wherein the cover has at least one slit near the proximal end portion to allow the cover to open.

5. The apparatus of claim 1, wherein one or more of the plurality of struts are configured to expand in a predetermined manner.

6. The apparatus of claim 5, wherein one or more of the plurality of struts have a notch at an internal face of a desired bending point to facilitate expansion of the expandable member in the predetermined manner.

7. The apparatus of claim 1, wherein some of the plurality of struts extend from the distal end portion and some of the plurality of struts extend from the proximal end portion, and the prosthetic device is removably coupled at a first end to the struts that extend from the distal end portion and at a second end to the struts that extend from the proximal end portion.

8. An apparatus for delivering a prosthetic device through the vasculature of a patient comprising:
   an elongate shaft having a distal end; and
   a radially expandable member coupled to the distal end of the elongate shaft, the expandable member having an open frame configuration and an outer mounting surface for mounting the prosthetic device in a collapsed state thereon,
   wherein the expandable member is configured to expand radially outwards from a first configuration to a second configuration to expand the prosthetic device, and
   wherein the expandable member comprises a cover that at least partially surrounds the plurality of struts, and wherein the cover is configured to open to permit fluid to flow through the expandable member from the distal end portion to the proximal end portion and to close to substantially prevent fluid from flowing through the expandable member from the proximal end portion to the distal end portion.

9. The apparatus of claim 8, wherein the expandable member comprises a screw member that extends between the distal end portion and the proximal end portion, and rotation of the screw member causes the distal end and proximal end portions to move closer together and causes the plurality of struts to expand radially.

10. The apparatus of claim 8, wherein the expandable member comprises a plurality of longitudinally extending struts that extend between a distal end portion and a proximal end portion.

11. The apparatus of claim 10, wherein one or more of the plurality of struts are configured to expand in a predetermined manner.

12. The apparatus of claim 8, further comprising an anchoring device, the anchoring device having a plurality of members that are moveable between a first unexpanded state and a second expanded state.

* * * * *